United States Patent [19]
Fujimiya et al.

[11] Patent Number: 6,093,694
[45] Date of Patent: Jul. 25, 2000

[54] ANTITUMOR ACTIVE SUBSTANCES

[75] Inventors: Yoshiaki Fujimiya, Ibaraki; Takusaburo Ebina, Sendai, both of Japan

[73] Assignee: Sumitomo Forestry Co., Ltd., Japan

[21] Appl. No.: 09/319,971

[22] PCT Filed: Nov. 28, 1997

[86] PCT No.: PCT/JP97/04352

§ 371 Date: Jun. 14, 1999

§ 102(e) Date: Jun. 14, 1999

[87] PCT Pub. No.: WO98/27992

PCT Pub. Date: Jul. 2, 1998

[30] Foreign Application Priority Data

Dec. 20, 1996 [JP] Japan ..................... 8-342025

[51] Int. Cl.[7] .......................... A61K 38/16; A61K 38/14; C07K 14/00
[52] U.S. Cl. ................. 514/8; 530/322; 530/395
[58] Field of Search .................. 424/195; 514/8, 514/54; 530/395, 322, 396, 397

[56] References Cited

FOREIGN PATENT DOCUMENTS

| 55-108292 | of 1980 | Japan . |
|---|---|---|
| 55-74797 | of 1980 | Japan . |
| 64-66127 | of 1989 | Japan . |
| 64-67194 | of 1989 | Japan . |
| 64-67195 | of 1989 | Japan . |
| 2-211847 | of 1990 | Japan . |
| 2-78630 | of 1990 | Japan . |
| 6-9423 | of 1994 | Japan . |
| 8-165302 | of 1996 | Japan . |

OTHER PUBLICATIONS

Kawagishi et al. Fractionation and Antitumor Activity of the Water–Insoluble Residue of *Agaricus blazei* Fruiting Bodies: Carbohydrate Research, vol. 186 pp. 267–273, 1989.

*Primary Examiner*—Jean C. Witz
*Assistant Examiner*—Patricia Patten
*Attorney, Agent, or Firm*—Pollock, Vande Sande & Amernick, R.L.L.P.

[57] ABSTRACT

By extracting hot water-insoluble and ethanol-insoluble components of the fruit body of Agaricus blazei Murill belonging to the genus Agaricus with 5% ammonium oxalate aqueous solution, degrading the extract with hydrochloric acid and then purifying the acid-degraded product through gel permeation and affinity chromatography, there are obtained the antitumor-active substances having a weight-average molecular weight of $38 \times 10^4$ daltons and a dispersion degree of 2.3, a weight-average molecular weight of $29 \times 10^4$ daltons and a dispersion degree of 7.3, a weight-average molecular weight of $2.4 \times 10^4$ daltons and a dispersion degree of 4.1, and a weight-average molecular weight of $2.0 \times 10^4$ daltons and a dispersion degree of 3.6. These substances exhibit a significant antitumor effect against solid tumor, when determined by gel permeation.

15 Claims, 9 Drawing Sheets

GPC FRACTION OF ACID-DEGRADED PRODUCT

DEAE FRACTION OF HIGH MOLECULAR COMPONENT (FRACTION a)

DEAE FRACTION OF LOW MOLECULAR COMPONENT (FRACTION b)

¹H-NMR SPECTRUM OF THE ANTITUMOR-ACTIVE SUBSTANCE OF THIS INVENTION

ANTITUMOR ACTIVE SUBSTANCES

FIELD OF THE INVENTION

The present invention relates to a substance having an antitumor activity and, an antitumor composition and a health food, comprising the same. More particularly, the present invention relates to a substance having an antitumor activity, which substance is obtainable by collecting the extract residues with ethanol from the fruit body of Agaricus blazei Murill belonging to the genus Agaricus, degrading the residues with an acid and then purifying the acid-degraded product. The present invention further relates to an antitumor composition and a health food comprising such an antitumor-active substance.

BACKGROUND ART

Agaricus blazei Murill belonging to the genus Agaricus and also called himemaitsutake mushroom is a kind of mushrooms that grows wild mainly in the mountainous region of the southeastern Brazil, Sao Paulo. The natives have long been using Agaricus blazei Murill as an edible mushroom.

In these years, Agaricus blazei Murill has become widely cultured also in Japan to make its extracts available for the treatment of diabetes and hypertension.

Various investigations have been made to explore substances having an antitumor activity. It is reported that polysaccharides with an antitumor activity are obtained, for example, by extracting the fruit body or mycelium of Agaricus blazei Murill with an aqueous medium (Japanese Patent KOKAI (Laid-Open) Nos. 55-74797, 64-67194, 64-67195, 55-108292, etc.). It is also reported that a nucleic acid component having an antitumor activity is extracted from the fruit body of himematsutake mushroom (Japanese Patent KOKAI (Laid-Open) No. 64-66127). These substances having an antitumor activity are all extracted from the components soluble in an aqueous medium or soluble in hot water.

On the other hand, Japanese Patent Application KOKAI No. 2-78630 discloses that a proteoglycan having an antitumor activity was isolated from the extract residue of the Agaricus blazei Murill fruit body with hot water. More specifically, it is reported that the Agaricus blazei Murill fruit body was extracted with hot water to remove water-soluble components, the resulting residue was further extracted with hot 1% ammonium oxalate aqueous solution; then the extract residue gave the proteoglycan having an antitumor activity.

The substances mentioned above are obtained either from the components soluble in an aqueous medium or soluble in hot water, or from the extract residue with hot water. Thus these substances are all derived from the components insoluble in hot 1% ammonium oxalate aqueous solution.

On the other hand, the present inventors found that a substance having an antitumor activity was obtained from the extract residue of the Agaricus blazei Murill fruit body with hot water followed by further extraction with hot 1% ammonium oxalate aqueous solution. Japanese Patent Application No. 4-160924 (Japanese Patent KOKAI (Laid-Open) No. 6-9423) is directed to the substance.

However, this substance is not satisfactory for the treatment of solid tumor since its antitumor activity is not sufficiently potent.

Either the above substance obtained from the components of the Agaricus blazei Murill fruit body soluble in an aqueous medium or soluble in hot water or the substance insoluble in hot 1% ammonium oxalate aqueous solution which is obtained from the extract residue with hot water is yet insufficient in their antitumor activity.

DESCRIPTION OF THE INVENTION

The present inventors have found that a substance having a potent antitumor activity can be obtained by treating the Agaricus blazei Murill fruit body with hot ethanol, collecting the extract residues, degrading the residues with an acid, preferably after extracting with ammonium oxalate, or directly without ammonium oxalate extraction, and then purifying the acid degradation product. The inventors have further found that the substance is useful as an active ingredient of an antitumor composition and of a health food. The present invention has thus been accomplished.

The present invention relates to a substance having an antitumor activity, which is obtainable from the fruit body of Agaricus blazei Murill belonging to the genus Agaricus by acid degradation of the components of the fruit body which are insoluble in hot water and insoluble in ethanol, followed by purification; the substance being preferably obtainable from the fruit body by extracting the insoluble components with an ammonium oxalate aqueous solution, degrading the extract with an acid and then purifying the acid-degraded product, which substance has a weight-average molecular weight of $38 \times 10^4$ daltons and a dispersion degree of 2.3, an average molecular weight of $29 \times 10^4$ daltons and a dispersion degree of 7.3, an average molecular weight of $2.4 \times 10^4$ daltons and a dispersion degree of 4.1, or an average molecular weight of $2.0 \times 10^4$ daltons and a dispersion degree of 3.6, when measured by gel permeation.

The present invention further relates to an antitumor composition comprising as an active ingredient the antitumor-active substance described above.

The present invention further relates to a health food comprising as an active ingredient the antitumor-active substance described above.

BEST MODE FOR CARRYING OUT THE INVENTION

Figure 1:
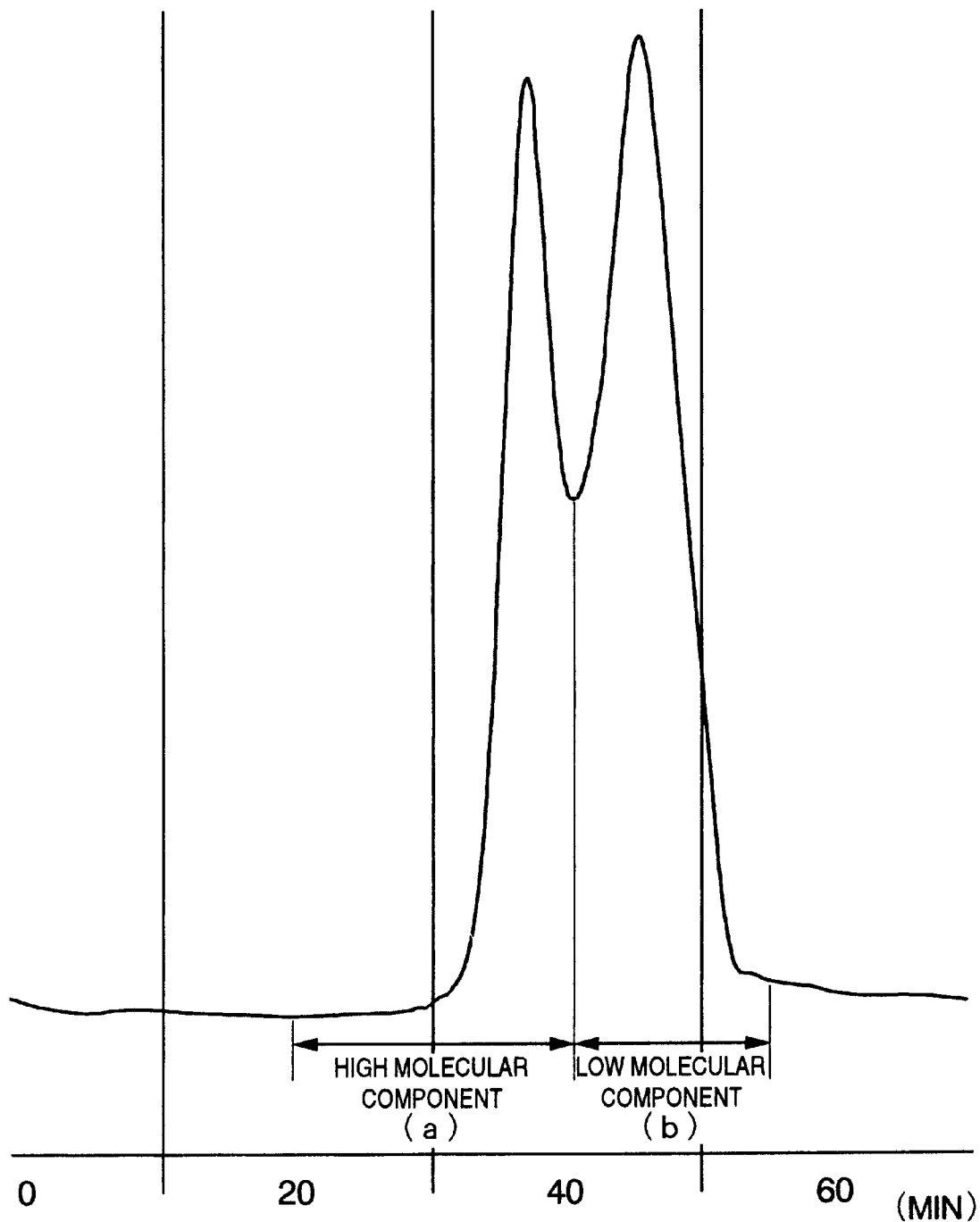
FIG. 1 shows a profile of chromatogram obtained when the acid degradation product of the Agaricus blazei Murill fruit body was subjected to gel permeation.

Agaricus blazei Murill belonging to the genus Agaricus is already known widely and has been deposited in Fermentation Research Institute of the Agency of Industrial Science & Technology of Japan under Accession No. 4731. Known species other than the deposited Agaricus blazei Murill may of course be employed in the present invention.

To obtain the antitumor-active substances of the present invention from the fruit body of Agaricus blazei Murill, the following procedures are used.

The fruit body may be fresh or dry. In general, the fresh fruit body is cut into thin strips and the dry one is finely grounded for use.

First, the fruit body is treated with 75–90% hot ethanol, preferably 80–85%, e.g., 80% hot ethanol to remove soluble components. The residues are collected. The temperature is generally kept at about 80° C. The treatment is generally carried out for 6 to 24 hours, preferably about 18 to 22 hours, though the treating time may vary depending upon an amount of the fruit body to be treated. By such a treatment, low molecular organic compound components are removed.

Subsequently, the resulting residue is treated with hot water to remove components soluble in hot water. The residues are again collected, whereby neutral and acidic polysaccharides soluble in hot water are removed. The temperature of hot water used for the treatment ranges generally from 80 to 100° C. The time required for the treatment is generally between 6 and 24 hours, preferably between 18 and 22 hours.

The collected residues are then freeze-dried and used for the next step of acid degradation. Preferably, the collected residues are extracted with 1–5%, preferably 5% hot ammonium oxalate aqueous solution to recover the components soluble in the ammonium oxalate aqueous solution. The extraction is normally carried out while boiling the ammonium oxalate aqueous solution. The thus recovered components are collected and concentrated. After the concentration, ammonium oxalate is subjected to gel permeation for desalting and concentration, followed by freeze drying.

The freeze-dried product is then subjected to acid degradation. For the acid degradation, strong acids such as hydrochloric acid, sulfuric acid, nitric acid, etc. may preferably be used. Of these acids, hydrochloric acid is particularly preferred. More specifically, the freeze-dried product is dissolved in 1N hydrochloric acid and the solution is allowed to stand overnight at room temperature, whereby acid degradation can be effected.

Following the acid degradation, the degradation product is neutralized with, e.g., 1N sodium hydroxide aqueous solution. The resulting aqueous solution is centrifuged to remove unwanted matters. The supernatant is desalted and concentrated through a ultrafiltration membrane, freeze-dried and then purified.

The freeze-dried acid degradation product thus obtained may be purified by gel permeation and affinity chromatography. Gel permeation may be performed using, e.g., GPC column or TSKgel G 5000 PW connected with TSKgel G 3000PW (each 21.5 mm×300 mm, made bay Toso Co., Ltd.). The acid degradation product is separated by gel permeation into a high molecular fraction with a molecular weight of approximately $10^5$ to $10^6$ daltons and a low molecular fraction with a molecular weight of approximately $5 \times 10^3$ to $5 \times 10^4$ daltons.

Next, the high and low molecular fractions thus obtained are subjected to affinity chromatography, respectively, for purification. Thus, the antitumor-active substance having a weight-average molecular weight of $29 \times 10^4$ daltons and a dispersion degree of 7.3, and the antitumor-active substances having a weight-average molecular weight of $2.4 \times 10^4$ daltons and a dispersion degree of 4.1 and having a weight-average molecular weight of $2.0 \times 10^4$ daltons and a dispersion degree of 3.6 may be obtained from the high and low molecular fractions, respectively.

The affinity chromatography may be performed using, e.g., a DEAE column or TSKgel DEAE-5PW (21.5 mm×150 mm×2, made bay Toso Co., Ltd.). The antitumor-active substance having a weight-average molecular weight of $29 \times 10^4$ daltons and a dispersion degree of 7.3 according to the present invention may be obtained by adsorbing the high molecular fraction described above to a DEAE column and then eluting with 0.5M NaCl aqueous solution. The antitumor-active substance having a weight-average molecular weight of $2.4 \times 10^4$ daltons and a dispersion degree of 4.1 may be obtained by adsorbing the low molecular fraction described above to a DEAE column and then eluting with 0.2M NaCl aqueous solution. The antitumor-active substance having a weight-average molecular weight of $2.0 \times 10^4$ daltons and a dispersion degree of 3.6 may be obtained by eluting with 0.5M NaCl aqueous solution.

The antitumor-active substance having a weight-average molecular weight of $29 \times 10^4$ daltons and a dispersion degree of 7.3 according to the present invention has an ivory white color and is cotton-like, highly hygroscopic and water-soluble. The antitumor-active substance having a weight-average molecular weight of $2.4 \times 10^4$ daltons and a dispersion degree of 4.1 and the antitumor-active substance having a weight-average molecular weight of $2.0 \times 10^4$ daltons and a dispersion degree of 3.6 are brown, hygroscopic and water-soluble.

The antitumor-active substance having a weight-average molecular weight of $29 \times 10^4$ daltons and a dispersion degree of 7.3 has a small absorption at UV of 280 nm; it is thus considered that the substance would be mainly composed of polysaccharides or contain in part some proteoglycans. The antitumor-active substance having a weight-average molecular weight of $2.4 \times 10^4$ daltons and a dispersion degree of 4.1 has a slight absorption at UV of 280 nm; it is thus considered that the substance would be mostly composed of polysaccharides. The antitumor-active substance having a weight-average molecular weight of $2.0 \times 10^4$ daltons and a dispersion degree of 3.6 has a considerable absorption at UV of 280 nm; it is thus considered that the substance would be a complex mainly composed of proteins, to a part of which polysaccharides are conjugated.

The antitumor-active substance having a weight-average molecular weight of $38 \times 10^4$ daltons and a dispersion degree of 2.3 according to the present invention may be obtained by further purifying the aforesaid antitumor-active substance having a weight-average molecular weight of $29 \times 10^4$ daltons and a dispersion degree of 7.3 by gel permeation using, e.g., a GPC column for desalting and concentration.

The antitumor-active substance having a weight-average molecular weight of $38 \times 10^4$ daltons and a dispersion degree of 2.3 in accordance with the present invention is ivory white, cotton-like, highly hygroscopic and water-soluble. Observation of one-dimensional proton spectrum at the anomeric proton region of the antitumor-active substance of the present invention through measurements of $^1$H-NMR and $^{13}$C-NMR indicates that there are peaks at 5.27 ppm and 4.51 ppm. The peaks observed at 5.27 ppm and 4.51 ppm designate 1-4-α-glucan and 1-6β-glucan, respectively. Integration of the peaks observed by NMR reveals that a ratio of 1-4-α-glucan to 1-6-β-glucan is 4:1. Therefore, the antitumor-active substance of the present invention is a polysaccharide mainly composed of 1-4-α-glucan and 1-6-β-glucan. In addition, IR analysis of the antitumor-active substance of the present invention indicates that there an absorption appears at 881 cm$^{-1}$. Thus, its specific rotary power is found to be $[\alpha]^{20}_D +121°$.

The antitumor-active substances of the present invention exhibit a potent antitumor activity against, e.g., fibrosarcoma-derived Meth-A. Among solid cancers, Meth-A tumor cells are known to be most resistant to chemotherapeutic agents (Biotherapy, 3(2), 557 (1989); Biotherapy, 4(4), 915 (1990); GAN-TO-KAGAKU RYOHO (Cancer and Chemotherapy), 18(11), 1812 (1991)). It is therefore expected that the substances of the present invention will be sufficiently effective to the solid cancers.

Where the antitumor-active substances of the present invention are used for therapy, the substances are administered orally or parenterally. For oral administration, tablets, capsules, granules, etc. are used. These pharmaceutical preparations may be prepared in a conventional manner. Parenteral preparations may also be prepared in a conventional manner, e.g., by dissolving or dispersing the antitumor-active substance in a vehicle for injection conventionally used.

A dose of the antitumor-active substances of the present invention may vary depending upon kinds of tumor, routes for administration, etc. but ranges normally from 5 to 100 mg/kg body weight.

The antitumor-active substance of the present invention may also be incorporated in a health food as an active ingredient. Where the antitumor-active substance of the present invention is used in a healthy food, dried raw materials are purified by the procedures described above, freeze-dried and incorporated into a food in a predetermined ratio, which is provided as foodstuffs. For example, the antitumor-active substances of the present invention may be used as a furikake or tastily seasoned dried food, as an ingredient of tea pack or in a capsule form. Furthermore, the freeze-dried or concentrated substance may be incorporated in dairy products, oil-and-fat products, seasonings, cakes, fruit juice, beverage, etc., for use. When added to these products, the amount of the substance of the present invention added to a health food is generally from 0.001 to 0.1 wt %.

By subjecting the extract of the hot water-insoluble and ethanol-insoluble components from the fruit body of Agaricus blazei Murill with 1–5% ammonium oxalate aqueous solution to acid degradation, the substances having a potent antitumor activity against solid tumor can be obtained.

Hereinafter, the present invention will be described in more detail, with reference to Examples.

EXAMPLE 1

Preparation of the antitumor-active substances (1) The fruit body (30 kg) of dried himematsutake mushroom is roughly ground into 5 mm or less. To 30 kg of the fruit body 270 liters of 80% v/v ethanol is added. The mixture is extracted while heating to reflux for 22 hours. After solid-liquid separation, 270 liters of 80% v/v ethanol is added to the residue. The resulting mixture is treated as described above. The procedure is repeated 3 times.

(2) After 270 liters of purified water is added to the extract residue (1) above, the mixture is extracted while heating to reflux for 22 hours, followed by solid-liquid separation. Next, 270 liters of purified water is added to the residue. The mixture is then treated as described above. The procedure is repeated 3 times.

(3) After 270 liters of 5% ammonium oxalate aqueous solution is added to the extract residue (2) above, the mixture is extracted while heating to reflux for 22 hours. After solid-liquid separation, the resulting aqueous solution was concentrated and 270 liters of 5% ammonium oxalate aqueous solution is added to the residue. The mixture is then treated as described above. The procedure is repeated 3 times. The extract of 800 liters in total is concentrated to 80–100 liters.

(4) The concentrated solution is filtered through a filter paper and then desalted/concentrated through a ultrafiltering membrane (fractional molecular weight of 10000). The concentrate is freeze-dried and dissolved in 1N HCl. After allowing to stand for 24 hours, the solution is neutralized with 1N NaOH aqueous solution to become pH of 7. The solution is centrifuged to remove unwanted matters. The supernatant is desalted and concentrated through a ultrafiltering membrane (fractional molecular weight of 10000) followed by freeze-drying.

(5) Following the acid degradation (4) described above, the purified dry powders are dissolved in 0.2M NaCl in a ratio of 10 mg/ml. After the powders are dissolved, the solution is centrifuged and the supernatant is filtered through a membrane filter of 0.8 μm.

The filtered supernatant is passed through a gel permeation column (TSKgel G 5000PW+TSKgel G 3000PW, each having a size of 5 mm×30 mm, connected columns). The dissolved components are separated into high and low molecular fractions by RI (differential refractometer). Each fraction is subjected to ultrafiltration (fractional molecular weight of 5000) for desalting and concentration. The high molecular concentrate fraction is passed through a DEAE column (TSKgel DEAE-5PW) followed by elution with 0.2M NaCl. After the eluate is removed, the residue is eluted with 0.5M NaCl followed by ultrafiltration for desalting. The aqueous solution prepared as above is found to have a potent antitumor activity. The low molecular concentrate fraction is passed through the same column to remove water-soluble matters. The eluates obtained by eluting with 0.2M NaCl and 0.5M NaCl are subjected to ultrafiltration for desalting. The aqueous solution prepared as above is found to have a potent antitumor activity.

The purified high molecular concentrate fraction is passed through a gel permeation column as described above. The eluate is desalted by ultrafiltration and then concentrated. The substance is found to have a more potent antitumor activity.

(6) The step (5) described above is shown in Table 1 below in more detail. After the acid degradation, high molecular components (a) and low molecular components (b) are obtained by gel permeation. The components (a) and (b) are further subjected to affinity chromatography to give high molecular component, a-3, low molecular components, b-2 and b-3. The high molecular component, a-3 is further passed through a gel permeation column to give purified product, H-3. The antitumor-active substances of the present invention are the high molecular component, a-3, the low molecular components, b-2 and b-3 and the purified product, H-3.

TABLE 1

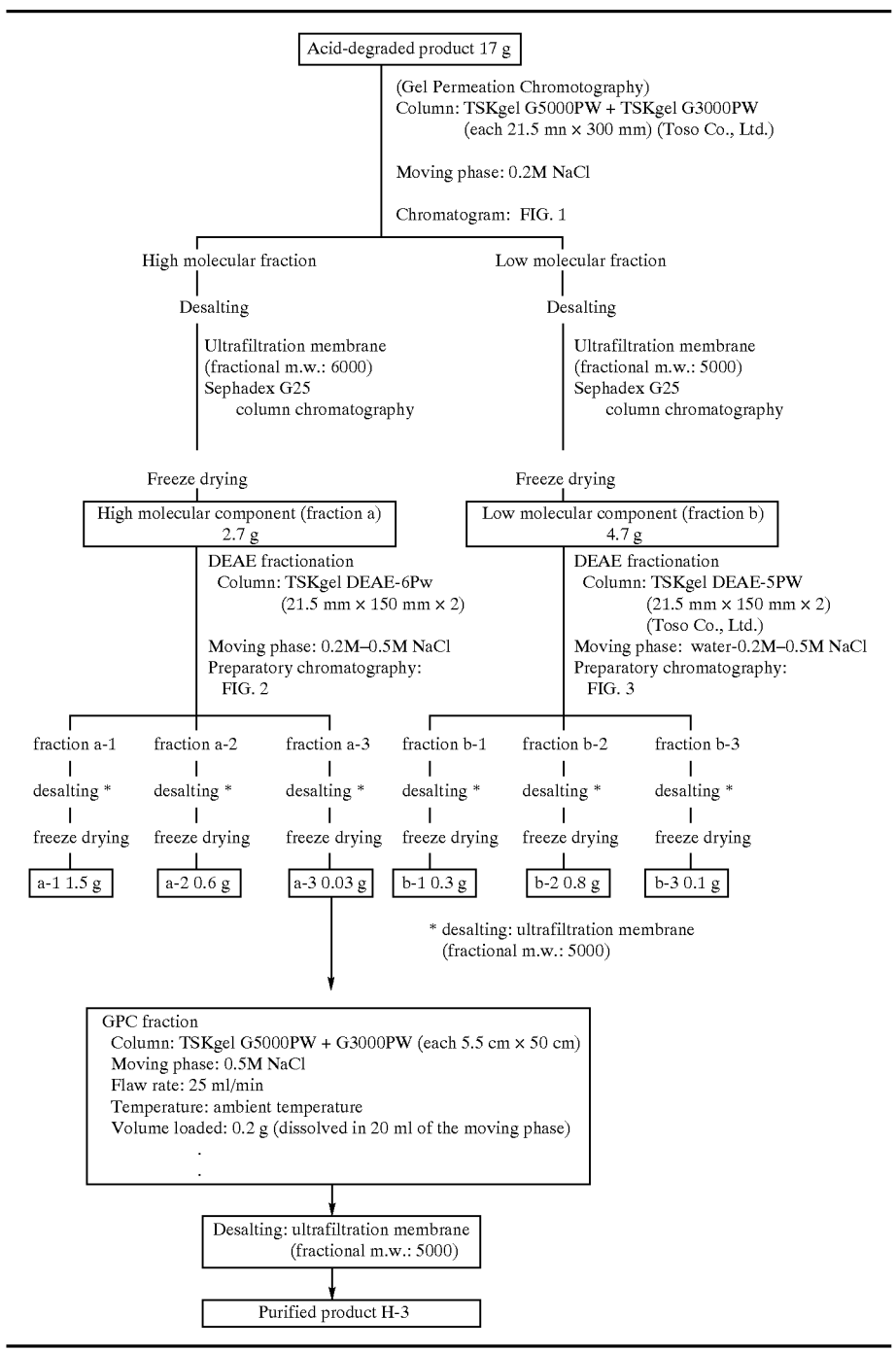

Figure 2:
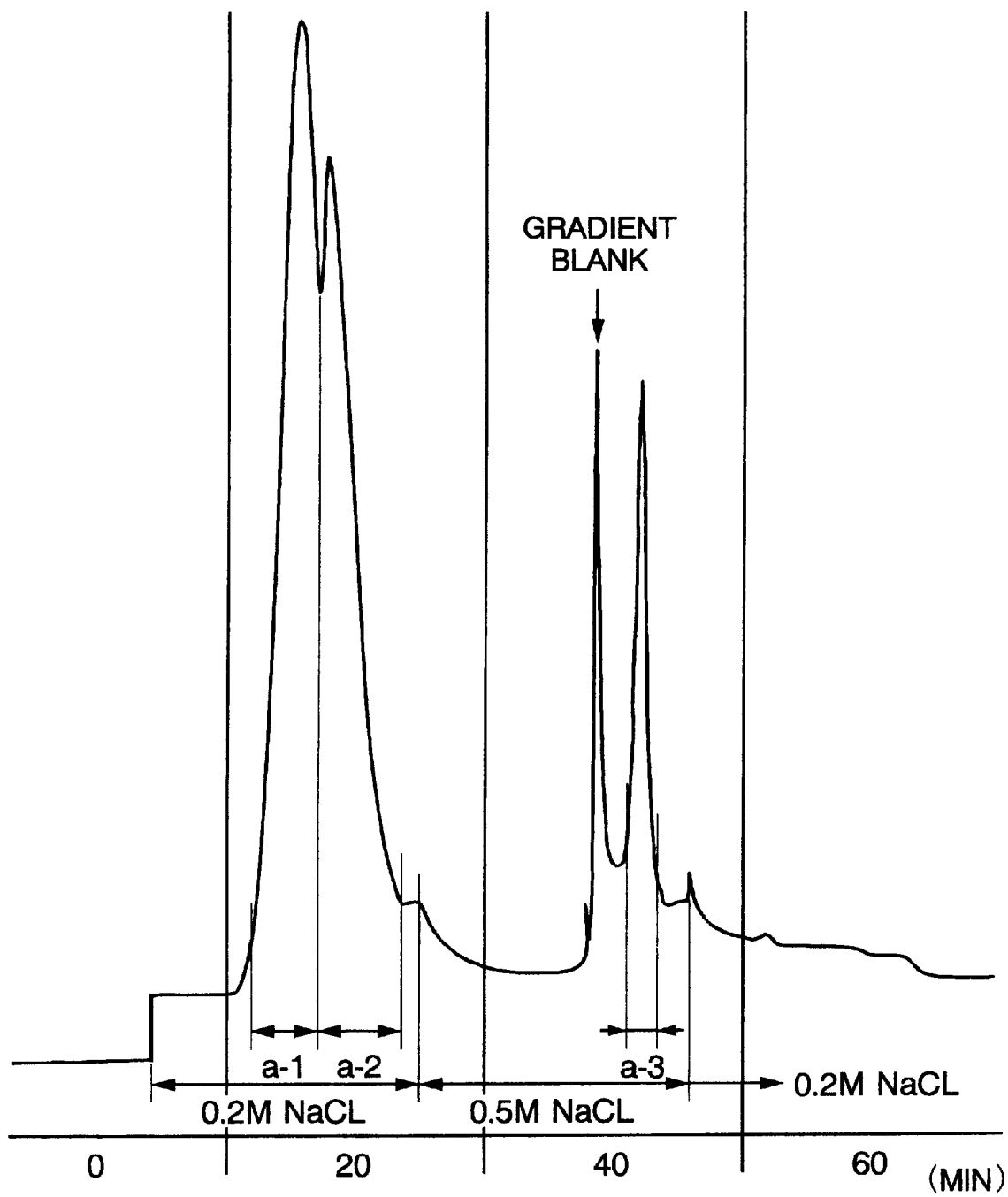
FIG. 2 shows a profile obtained when the high molecular component resulting from the gel permeation shown in FIG. 1 was subjected to affinity chromatography (DEAE fraction).
Figure 3:
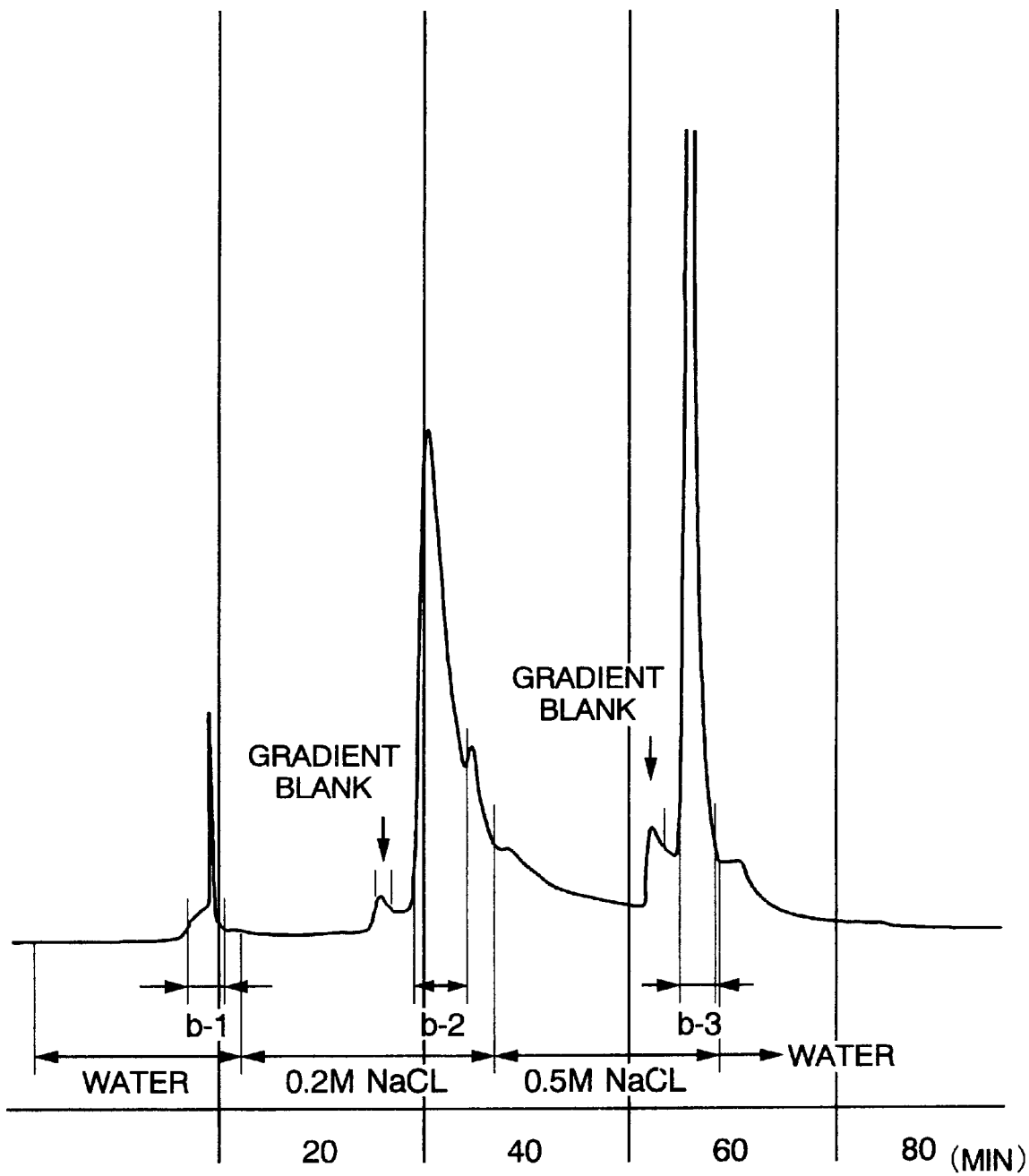
FIG. 3 shows a profile obtained when the low molecular component resulting from the gel permeation shown in FIG. 2 was subjected to affinity chromatography (DEAE fraction).

As indicated in Table 1, the profile of chromatogram obtained by gel permeation (GPC fractionation) is shown in FIG. 1. In FIGS. 2 and 3, profiles obtained when the high and low molecular component fractions obtained by gel permeation are subjected to affinity chromatography (DEAE fraction) are shown, respectively.

Figure 4:
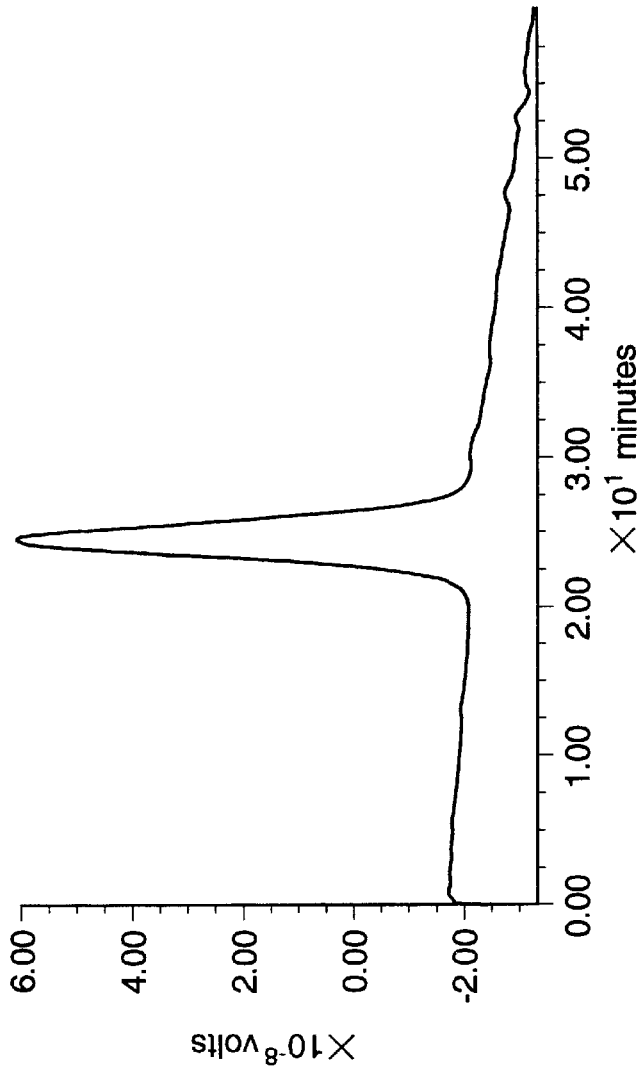
FIG. 4 shows a profile of chromatogram obtained when the antitumor-active substance of the present invention was subjected to gel permeation.
Figure 5:
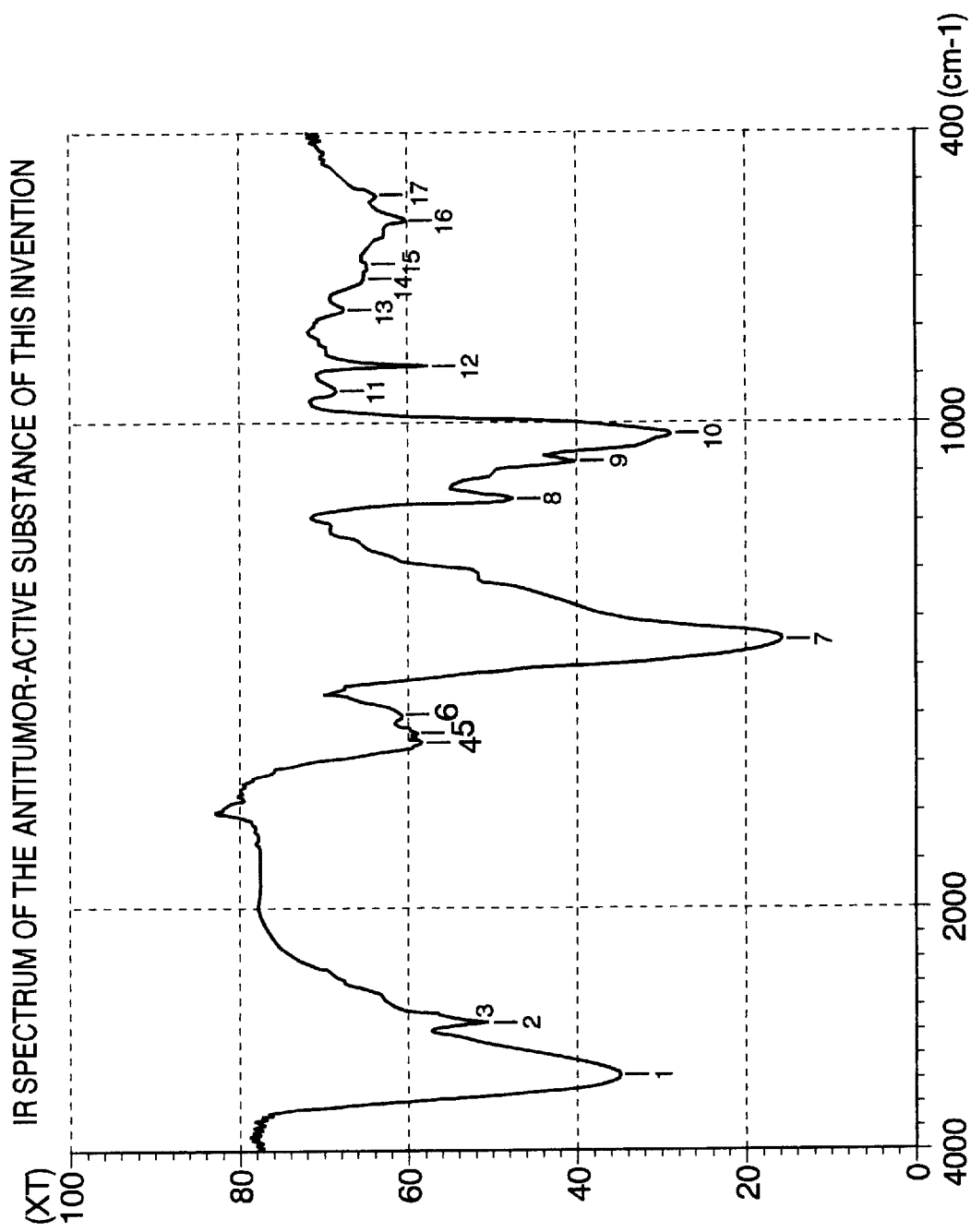
FIG. 5 shows an IR spectrum of the antitumor-active substance of the present invention.

When the high molecular component a-3 shown in Table 1 is subjected to gel permeation (GPC fractionation) for further purification, the purified product H-3 is obtained. The profile of chromatogram by the GPC fractionation is shown in FIG. 4.

(7) With regard to the acid-degraded product, high molecular component (a) and low molecular component (b) obtained by gel permeation, high molecular components, a-1, a-2 and a-3 and low molecular components, b-1, b-2 and b-3 obtained by affinity chromatography and purified product H-3, all shown in Table 1, gel permeation analysis was performed. The results are shown in Table 2.

TABLE 2

Results of gel permeation analysis

| Component | Number-average molecular weight | Weight-average molecular weight | Dispersion degree | Peak maximum |
|---|---|---|---|---|
| Acid degraded product | $0.8 \times 10^4$ | $17 \times 10^4$ | 20 | $27 \times 10^4, 1.3 \times 10^4$ |
| High molecular component (a) | $10 \times 10^4$ | $35 \times 10^4$ | 3.4 | $31 \times 10^4$ |
| Low molecular component (b) | $0.3 \times 10^4$ | $2.7 \times 10^4$ | 8.0 | $1.2 \times 10^4$ |
| High molecular components | | | | |
| a-1 | $18 \times 10^4$ | $39 \times 10^4$ | 2.4 | $35 \times 10^4$ |
| a-2 | $8.2 \times 10^4$ | $28 \times 10^4$ | 3.2 | $26 \times 10^4$ |
| a-3 | $4.0 \times 10^4$ | $29 \times 10^4$ | 7.8 | $32 \times 10^4$ |
| Low molecular components | | | | |
| b-1 | $0.8 \times 10^4$ | $2.4 \times 10^4$ | 3.0 | $0.7 \times 10^4$ |
| b-2 | $0.6 \times 10^4$ | $2.4 \times 10^4$ | 4.1 | $1.7 \times 10^4$ |
| b-3 | $0.6 \times 10^4$ | $2.0 \times 10^4$ | 3.8 | $1.7 \times 10^4$ |
| Purified product H-3 | $17 \times 10^4$ | $38 \times 10^4$ | 2.3 | $30 \times 10^4$ |

Conditions for gel permeation analysis:
Column: TSKgel G5000PW +TSKgel G3000PW (each 21.5 mm×300 mm)
Detection: RI
Column temperature: 40° C.
Moving phase: 50 mM sodium nitrate
Flow rate: 0.5 ml/min
Volume loaded: 200 µl (ca. 1 mg/ml, moving phase)
Molecular weight calibration: pullulan
(Shodex: $0.58 \times 10^1$, $1.22 \times 10^4$, $2.37 \times 10^4$, $4.80 \times 10^4$, $10.0 \times 10^4$, $18.6 \times 10^4$, $38.6 \times 10^4$, $85.3 \times 10^4$)

The antitumor-active substance of the present invention having an average molecular weight of $29 \times 10^4$ daltons and a dispersion degree of 7.3 corresponds to the high molecular component, a-3 shown in Tables 1 and 2. The antitumor-active substances of the present invention having a weight-average molecular weight of $2.4 \times 10^4$ daltons and a dispersion degree of 4.1 and having a weight-average molecular weight of $2.0 \times 10^4$ daltons and a dispersion degree of 3.6 correspond to the low molecular components, b-2 and b-3, respectively, shown in Tables 1 and 2.

The antitumor-active substance of the present invention having a weight-average molecular weight of $38 \times 10^4$ daltons and a dispersion degree of 2.3 corresponds to the purified product H-3 obtained by purifying the high molecular component a-3 shown in Tables 1 and 2 through gel permeation, desalting and concentration.

(8) With respect to the purified product H-3 of the present invention, IR was determined by the KBr tablet method. The resulting IR spectrum is shown in Table 5. The spectrum reveals that an absorption appears at 881 cm$^{-1}$. It is assumed that the absorption would be derived from B-D-gluropyrano bond.

Figure 6A:
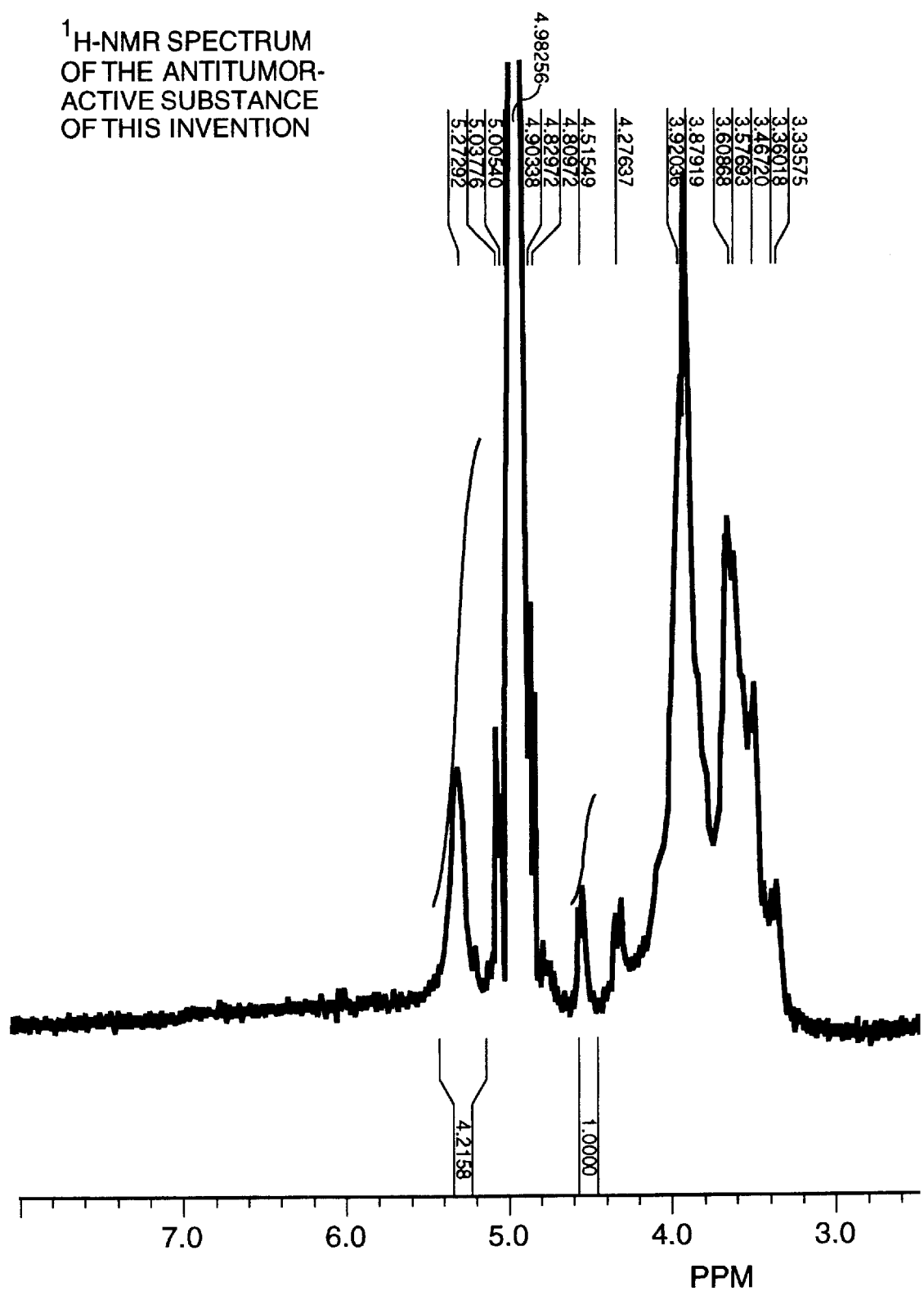
FIG. 6A and FIG. 6B show a one-dimensional proton NMR spectrum of the antitumor-active substance of the present invention.
Figure 6B:

With respect to the purified product H-3, one-dimensional?? NMR spectrum ($^1$H-NMR, $^{13}$C-NMR) was measured by AC-300P manufactured by BRUKER Co., Ltd. The measurement temperature was 298K. The one-dimensional proton NMR-spectrum is shown in FIG. 6. In the one-dimensional spectrum, peaks are observed at 5.27 ppm and 4.51 ppm in the proton region. It is considered from the data shown in literature (Agric. Biol. Chem., 54, 2889 (1990)) that the peak at 5.27 ppm would be derived from 1-4-α-glucan and the peak at 4.51 ppm would be from 1-6-β-glucan. The integrated data reasonably indicates that a ratio of 1-4-α-glucan to 1-6-β-glucan is 4:1.

With respect to the purified product H-3, its optical rotation was determined at 20° C. and a layer length?? of 50 mm in a concentration of 1% in 1% sodium hydroxide aqueous solution, using D-line of sodium spectrum. The specific rotary power was found to be $[\alpha]^{20}_D + 121°$.

(9) With respect to the purified product H-3, all sugars were determined by the phenol-sulfate method. The sugar content (%) in the purified H-3 product was 90.0%.

Furthermore, a sample (5 ml) from the purified H-3 product was hydrolyzed (100° C., 3 hours) with 2M trifluoroacetic acid (2 ml). After distillation in vacuo, the constituent sugars were determined using an amino column (CAPCELL PAK, NH$_2$ (4.6 mm×250 mm)). Only glucose was detected.

(10) The protein content of the purified H-3 product was determined by the Lowry method. Bovine albumin was used as a standard. The protein content (%) of H-3 was found to be 3.4%.

After 8 mg of the purified H-3 product was hydrolyzed (110° C., 22 hours) with 6N hydrochloric acid (2 ml), its constituent amino acids were determined using HPLC (Hitachi, Model L-8500 type amino acid analyzer). The results are shown in Table 3.

TABLE 3

Composition of Amino Acids

| | Compositional ratio (% mol/mol) Purified H-3 Product |
|---|---|
| Asx | 10.4 |
| Thr | 5.7 |
| Ser | 7.6 |
| Glx | 11.4 |
| Gly | 9.3 |
| Ala | 10.3 |
| Val | 6.6 |
| (Cys)2 | 0.3 |
| Met | 1.2 |
| Ile | 5.0 |
| Leu | 9.3 |
| Tyr | 1.8 |
| Phe | 4.0 |
| Lys | 5.4 |
| His | 1.6 |
| Arg | 4.5 |
| Pro | 5.6 |
| Total | 100.0 |

The glucosamine content (%) detected was 0.06%.

EXAMPLE 2

Assay for antitumor activity

Meth-A (derived from fibrosarcoma) was simultaneously inoculated to mice (5 mice in one group, BALB/c, male mice of 6 weeks old) intradermally at the right flank (1×10$^6$) and left flank ($2\times10^5$) On Days 3, 4 and 5 after the inoculation, each of physiological saline solutions of the high molecular component a-3 and the low molecular components b-2 and b-3 obtained in Example 1, which are the antitumor-active substances of the present invention, was injected into the tumor at the same right flank (not injected into the tumor at the left flank) in a dose of 1 mg dry weight/mouse. For control, physiological saline alone was injected into the tumor at the right flank in another group of mice (control). For comparison in effects, the acid-degraded product prior to purification was injected into the right tumor in a further group of mice, following the schedule above.

A size (area) and weight of the tumor at the right flank and the left flank were measured at definite intervals up to Day 21 after the tumor inoculation, whereby the effects of the extracts obtained in Example 1 were examined.

The experimental results on Day 21 after the tumor inoculation are shown in Tables 4 and 5.

EXAMPLE 3

Assay for antitumor activity

Meth-A tumor cells (fibrosarcoma) were simultaneously inoculated on mice (5 mice in one group, BALB/c, male mice of 6 weeks old) intradermally at the right flank ($1\times10^6$) and left flank ($2\times10^5$). On Days 3, 4 and 5 after the inoculation, the antitumor-active substance (purified product, H-3) of the present invention obtained in Example 1 was injected into the tumor at the right flank, in the same schedule. For comparison in effects, the acid-degraded product prior to purification was also injected into the right tumor in another group of mice in the same schedule. For control, physiological saline alone was injected into the tumor at the right flank in another group of mice. A size (area, $mm^2$) of the tumor at the right flank and the left flank was measured every other day up to Day 21 after the tumor inoculation, whereby the effects of the extracts obtained in Example 1

TABLE 4

Antitumor effect of the high molecular component

| | | Tumor free/Total | Tumor Size ($mm^2$) | % inhibition | Tumor Weight (g ± S.D.) | % inhibition |
|---|---|---|---|---|---|---|
| High molecular component (a-1) | Right | 0/5 | 242.4 ± 97.37* | 52.5 | 1.4 ± 0.65 | 60.0 |
| | Left | 0/5 | 105.2 ± 93.26* | 63.0 | 0.5 ± 0.57 | 68.8 |
| High molecular component (a-2) | Right | 1/5 | 96.0 ± 162.72* | 61.6 | 1.3 ± 1.12 | 62.9 |
| | Left | 2/5 | 114.8 ± 132.82** | 56.9 | 0.7 ± 0.92 | 56.3 |
| High molecular component (a-3) | Right | 3/5 | 25.4 ± 31.11* | 95.1 | 0.1 ± 0.15 | 97.1 |
| | Left | 3/5 | 25.2 ± 35.27* | 91.1 | 0.6 ± 0.44 | 62.5 |
| Acid degraded product | Right | 0/5 | 265.0 ± 71.27* | 48.0 | 1.6 ± 0.57 | 53.3 |
| | Left | 0/5 | 149.2 ± 82.64* | 47.6 | 0.8 ± 0.45 | 50.0 |
| Control | Right | 0/5 | 510.0 ± 58.74 | N/A | 3.5 ± 0.52 | N/A |
| | Left | 0/5 | 284.4 ± 70.39 | N/A | 1.6 ± 0.32 | N/A |

Note: When compared to control,
*significant difference at $p < 0.01$
**significant difference at $p < 0.05$

TABLE 5

Antitumor effect of the low molecular component

| | | Tumor free/Total | Tumor Size ($mm^2$) | % inhibition | Tumor Weight (g ± S.D.) | % inhibition |
|---|---|---|---|---|---|---|
| Low molecular component (b-1) | Right | 0/5 | 470.2 ± 125.34⁺ | 5.3 | 3.1 ± 1.03 | 16.2 |
| | Left | 0/5 | 271.4 ± 87.90* | 17.1 | 1.9 ± 1.19 | 24.0 |
| Low molecular component (b-2) | Right | 1/5 | 131.8 ± 75.11* | 73.4 | 0.7 ± 0.39 | 81.0 |
| | Left | 1/5 | 143.2 ± 111.42* | 56.3 | 0.9 ± 0.68 | 54.0 |
| Low molecular component (b-3) | Right | 1/5 | 81.4 ± 45.78* | 83.6 | 0.5 ± 0.27 | 86.5 |
| | Left | 1/5 | 115.6 ± 117.33* | 64.7 | 0.7 ± 0.82 | 72.6 |
| Acid degraded product | Right | 0/5 | 288.8 ± 164.75* | 41.8 | 1.9 ± 1.24 | 48.6 |
| | Left | 3/5 | 74.4 ± 91.20* | 77.3 | 0.3 ± 0.50 | 88.0 |
| Control | Right | 0/5 | 496.4 ± 104.22 | N/A | 3.7 ± 0.75 | N/A |
| | Left | 0/5 | 327.4 ± 51.91 | N/A | 2.5 ± 0.76 | N/A |

Figure 7:
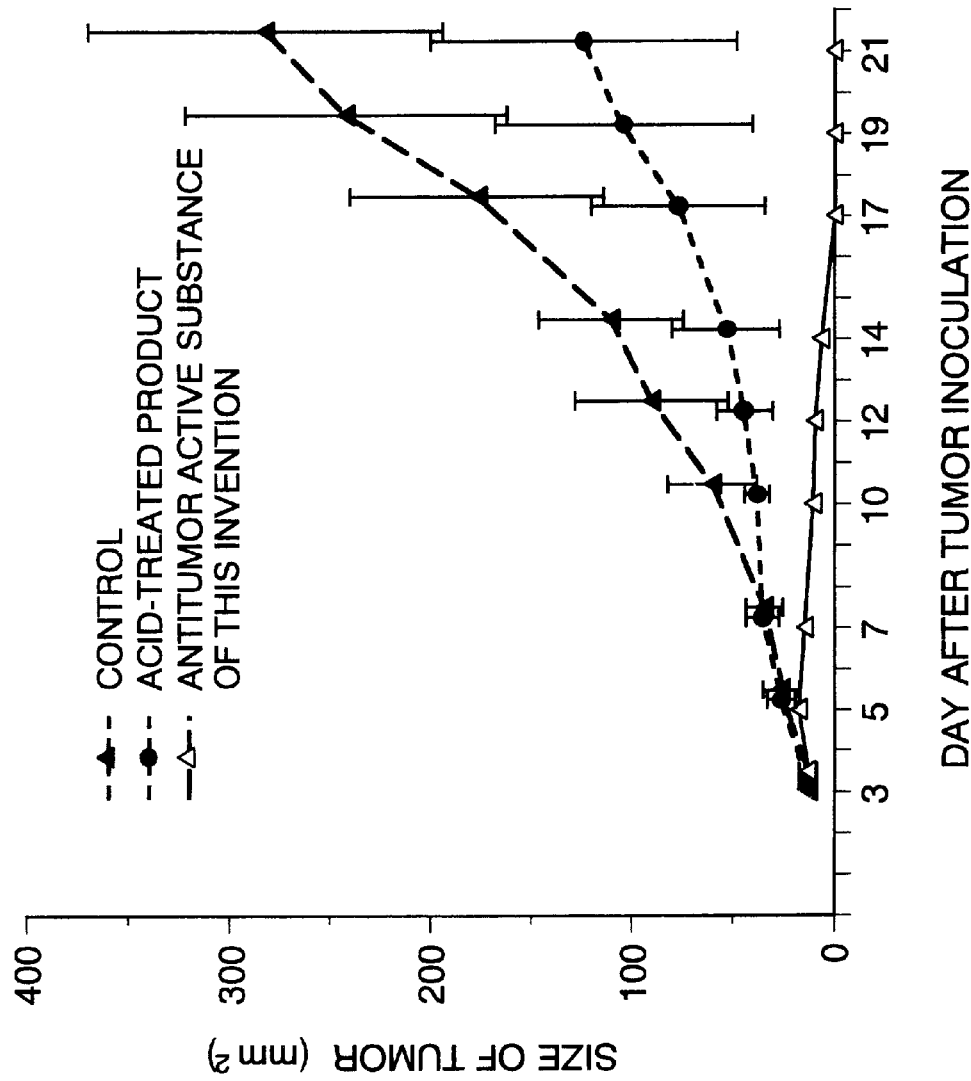
FIG. 7 shows an antitumor activity of the antitumor-active substance according to the present invention when mice were inoculated with Meth-A tumor cells intradermally in the right flank.
Figure 8:
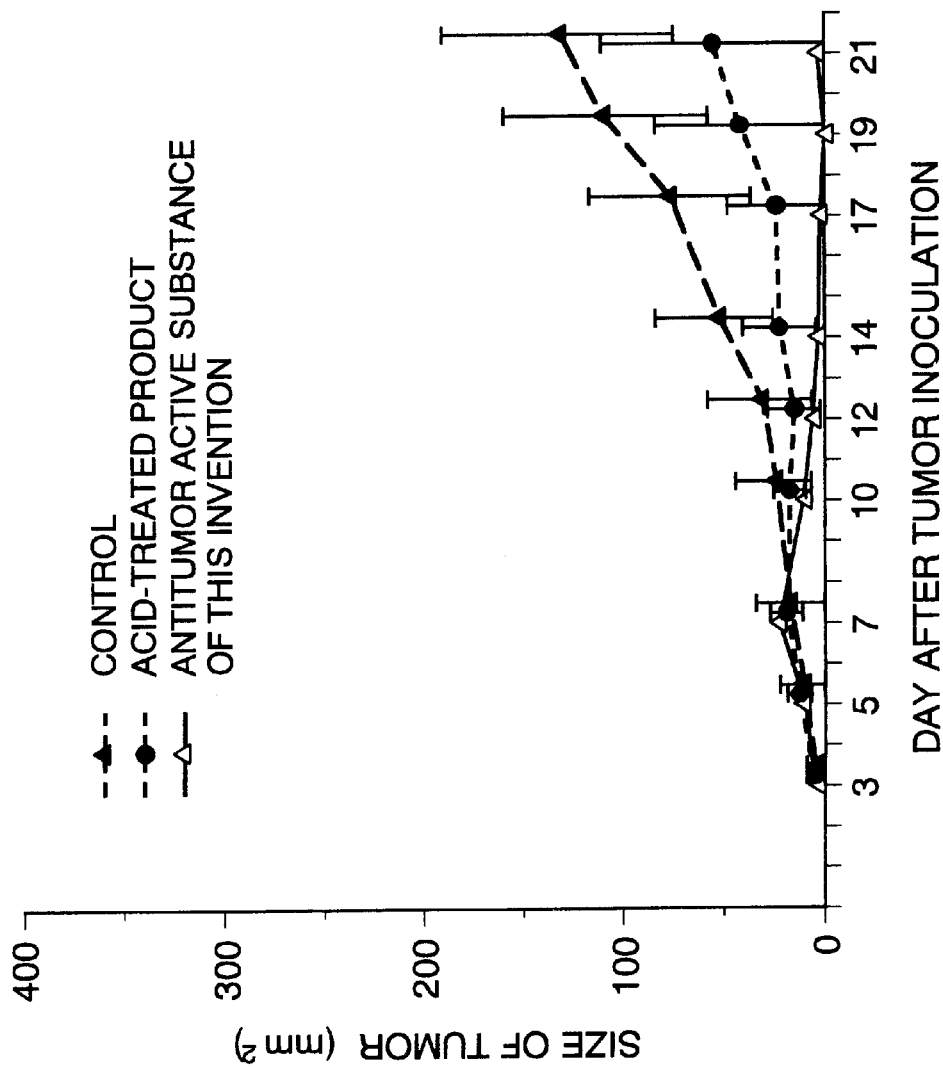
FIG. 8 shows an antitumor activity of the antitumor-active substance according to the present invention when mice were inoculated with Meth-A tumor cells intradermally in the left flank.

Note: When compared to control,
*significant difference at $p < 0.01$
**significant difference at $p < 0.05$ The results shown in Tables 4 and 5 reveal that the high molecular component a-3 and the low molecular components, b-2 and b-3 of the present invention exhibit a potent antitumor activity. When compared to control, the tumor growth at the left flank was also inhibited, though these components were not injected there. The results thus reveal that the substances of the present invention activated immunocompetent cells of host and the antitumor activity was exerted by the so activated immune function.

were examined. On Day 21, animals were sacrificed to weigh the tumors (g). The results of the tumor weight and size on Day 21 are shown in Table 6. In FIGS. 7 and 8, the experimental results obtained at the right and left flanks up to Day 21 after the tumor inoculation are shown, respectively. As is clearly noted from Table 6 and FIGS. 7 and 8, the antitumor-active substances of the present invention exhibit a potent antitumor activity against Meth-A tumor cells.

TABLE 6

| Antitumor-active | | Tumor free/ Total | Tumor Size (mm² ± S.D.) | % inhibition | Tumor Weight (g ± S.D.) | % inhibition |
|---|---|---|---|---|---|---|
| Purified product | Right | 5/5 | 0 ± 0*+ | 100.0 | 0 ± 0*+ | 100.0 |
| H-3 | Left | 4/5 | 2.4 ± 4.80*+ | 98.2 | <0.1*++ | ≧100.0 |
| Acid degraded | Right | 0/5 | 125.4 ± 77.55** | 55.7 | 0.8 ± 0.56** | 70.4 |
| product | Left | 2/5 | 55.6 ± 56.95*** | 58.8 | 0.3 ± 0.30** | 70.0 |
| Control | Right | 0/5 | 282.8 ± 88.38 | N/A | 2.7 ± 1.15 | N/A |
| | Left | 0/5 | 135.0 ± 57.12 | N/A | 1.0 ± 0.52 | N/A |

*$P < 0.01$ vs. Control
**$P < 0.01$ vs. Control
***$P < 0.05$ vs. Control
+$P < 0.01$ vs. acid-degraded fraction 3
++$P < 0.05$ vs. acid-degraded fraction 3
N/A: not applicable

EXAMPLE 4
Preparation of tablet

A mixture of 100 g of the antitumor-active substance (high molecular component, a-3) of the present invention obtained in Example 1, 100 g of mannitol and 100 g of glucose is tableted with a conventional tableting machine.

EXAMPLE 5
Preparation of tablet

A mixture of 100 g of the antitumor-active substance (purified product, H-3) of the present invention obtained in Example 1, 100 g of mannitol and 100 g of glucose is tableted with a conventional tableting machine.

EXAMPLE 6
Preparation of health food

After 1 liter of aqueous solution containing 1 mg of the antitumor-active substance (high molecular component, a-3) of the present invention obtained in Example 1 is added to a suitable amount of dextrin, the mixture is adsorbed to a base food.

The resulting powders are extruded into an extrusion granulator through a net of 1 mm. The granules are received on a 12 mesh sieve to sieve through.

The granules are dried at 60° C. overnight in a drier to give granules with about 3% moisture content. The granules are used as an additive to tea or the like.

EXAMPLE 7
Preparation of health food

After 1 liter of aqueous solution containing 1 mg of the antitumor-active substance (purified product H-3) of the present invention obtained in Example 1 is added to a suitable amount of dextrin, the mixture is adsorbed to a base food.

The resulting powders are extruded into an extrusion granulator through a net of 1 mm. The granules are received on a 12 mesh sieve to sieve through.

The granules are dried at 60° C. overnight in a drier to give granules with about 3% moisture content. The granules are used as an additive to tea or the like.

INDUSTRIAL APPLICABILITY

By degrading with an acid, the hot water-insoluble and ethanol-insoluble components of the fruit body of Agaricus blazei Murill belonging to the genus Agaricus, preferably by extracting the insoluble components with an ammonium oxalate aqueous solution, subjecting the extract to acid degradation, and then purifying the extract, the substances having a potent antitumor activity against solid cancer can be obtained.

What is claimed is:

1. An antitumor-active substance selected from the group consisting of:
   a substance having a molecular weight of $38 \times 10^4$ Daltons and a dispersion degree of 2.3,
   a substance having a molecular weight of $29 \times 10^4$ Daltons and a dispersion degree of 7.3,
   a substance having a molecular weight of $2.4 \times 10^4$ Daltons and a dispersion degree of 4.1 and
   a substance having a molecular weight of $2.0 \times 10^4$ Daltons and a dispersion degree of 3.6,
   said substance being obtainable by purification of the acid degraded product of the hot water-insoluble and ethanol-insoluble fraction of the fruit body of Agaricus blazei Murill belonging to the genus Agaricus.

2. The antitumor-active substance according to claim 1, which is obtainable by extracting the hot water-insoluble and ethanol-insoluble fraction of said fruit body with an ammonium oxalate aqueous solution, subjecting the extract to acid degradation and then purifying the acid-degraded product.

3. The antitumor-active substance according to claim 2, which has been purified by means of gel permeation followed by affinity chromatography.

4. The antitumor-active substance according to claim 2, wherein said antitumor-active substance has a weight-average molecular weight of $29 \times 10^4$ Daltons and a dispersion degree of 7.3, and is mainly composed of 1-4-p-glucan and 1-6-β-glucan in a ratio of 4:1.

5. An antitumor composition comprising as an active ingredient an effective amount of the antitumor-active substance according to claim 2 in combination with a pharmaceutically acceptable carrier.

6. A health food comprising as an active ingredient an effective amount of an antitumor-active substance according to claim 2.

7. The antitumor-active substance according to claim 1, which has been purified by means of gel permeation followed by affinity chromatography.

8. The antitumor-active substance according to claim 7, wherein said antitumor-active substance has a weight-average molecular weight of $29 \times 10^4$ Daltons and a dispersion degree of 7.3, and is mainly composed of 1-4-α-glucan and 1-6-β-glucan in a ratio of 4:1.

9. An antitumor composition comprising as an active ingredient an effective amount of the antitumor-active substance according to claim 7 in combination with a pharmaceutically acceptable carrier.

10. A health food comprising as an active ingredient an effective amount of an antitumor-active substance according to claim 7.

11. A health food comprising as an active ingredient an effective amount of an antitumor-active substance according to claim 7.

12. The antitumor-active substance according to claim 1 wherein said antitumor-active substance has a weight-average molecular weight of $29 \times 10^4$ Daltons and a dispersion degree of 7.3 and is mainly composed of 1-4-α-glucan and 1-6-β-glucan in a ratio of 1:4.

13. An antitumor composition comprising as an active ingredient an effective amount of the antitumor-active substance according to claim 12 in combination with a pharmaceutically acceptable carrier.

14. An antitumor composition comprising as an active ingredient, an effective amount of the antitumor-active substance in combination with a pharmaceutically acceptable carrier.

15. A health food comprising as an active ingredient, an effective amount of the antitumor-active substance according to claim 1.

* * * * *